United States Patent
Whitfield

[19]

[11] Patent Number: 6,151,721
[45] Date of Patent: Nov. 28, 2000

[54] NON-INVASIVE URINE COLLECTION DEVICE FOR FEMALES

[76] Inventor: Raymond W. Whitfield, 1925 Seward, 1E, Detroit, Mich. 48206

[21] Appl. No.: 09/546,296

[22] Filed: Apr. 10, 2000

[51] Int. Cl.[7] .............................. A47K 11/12; A61G 9/00
[52] U.S. Cl. ........................... 4/144.1; 4/144.3; 604/327
[58] Field of Search .................................. 4/144.1–144.4, 4/452; 604/327, 332, 337, 344, 389

[56] References Cited

U.S. PATENT DOCUMENTS

| | | | |
|---|---|---|---|
| 2,066,400 | 1/1937 | Hale | 4/144.3 |
| 3,131,403 | 5/1964 | Hill | 4/144.3 |
| 4,233,978 | 11/1980 | Hickey | 4/144.3 |
| 4,886,508 | 12/1989 | Washington | 604/327 |
| 5,053,027 | 10/1991 | Manfredi | 604/327 |
| 5,267,988 | 12/1993 | Farkas | 604/329 |
| 5,411,495 | 5/1995 | Willingham | 604/329 |
| 5,571,095 | 11/1996 | Lu | 604/329 |
| 5,632,736 | 5/1997 | Block | 4/144.3 |
| 5,735,835 | 4/1998 | Holland | 604/331 |
| 5,792,132 | 8/1998 | Garcia | 604/385.1 |

*Primary Examiner*—Charles R. Eloshway
*Attorney, Agent, or Firm*—Joseph N. Breaux

[57] ABSTRACT

A non-invasive urine collection device for females that includes an adhesive covered, flexible film patient attachment structure that is sealingly secured to the skin entirely around the pubic area of the patent so that urine eliminated in the normal manner enters a collecting member in connection with the patient attachment structure and is then transferred into a disposable urine collecting bottle.

1 Claim, 2 Drawing Sheets

NON-INVASIVE URINE COLLECTION DEVICE FOR FEMALES

TECHNICAL FIELD

The present invention relates to urine collecting devices and more particularly to a non-invasive urine collection device for females that includes an adhesive covered, flexible film patient attachment structure, a flexible plastic film urine collection funnel member and a disposable urine collection bottle; the adhesive covered, flexible film patient attachment structure having a urine collection opening formed therethrough that is reinforced around an internal perimeter edge thereof by a continuous section of closed cell foam and an exterior perimeter edge thereof totally surrounded by the adhesive covered, flexible film patient attachment structure; the flexible plastic film urine collection funnel member having a top edge in connection with the urine collection opening of the patient attachment structure such that a urine collecting cavity of the urine collection funnel member is in connection with the urine collection opening and a bottom urine discharge fitting formed through a bottom thereof in connection with a first end of a flexible plastic urine transfer tube; the disposable urine collection bottle being in fluid connection with a second end of the urine transfer tube; the adhesive covered, flexible film patient attachment structure being covered with a peel off cover member; the continuous section of closed cell foam having a number of slots formed into a lower portion thereof for allowing urine to flow therethrough and prevent puddling of urine from occurring; the urine collection opening being sized to fit entirely over a pubic hair covered area of a female user.

BACKGROUND ART

Because of the anatomical structure of females, it has been necessary to use invasive mechanisms, such as catheters, to drain urine from the bladder of bedridden female patients. Because this can lead to infection and is uncomfortable for most patients, it would be a benefit to have a non-invasive urine collection device for females that could be sealing secured entirely around the pubic area of the patent so that urine eliminated in the normal manner would enter a collecting member and then transferred into a disposable urine collecting bottle.

GENERAL SUMMARY DISCUSSION OF INVENTION

It is thus an object of the invention to provide a non-invasive urine collection device for females that includes an adhesive covered, flexible film patient attachment structure, a flexible plastic film urine collection funnel member and a disposable urine collection bottle; the adhesive covered, flexible film patient attachment structure having a urine collection opening formed therethrough that is reinforced around an internal perimeter edge thereof by a continuous section of closed cell foam and an exterior perimeter edge thereof totally surrounded by the adhesive covered, flexible film patient attachment structure; the flexible plastic film urine collection funnel member having a top edge in connection with the urine collection opening of the patient attachment structure such that a urine collecting cavity of the urine collection funnel member is in connection with the urine collection opening and a bottom urine discharge fitting formed through a bottom thereof in connection with a first end of a flexible plastic urine transfer tube; the disposable urine collection bottle being in fluid connection with a second end of the urine transfer tube; the adhesive covered, flexible film patient attachment structure being covered with a peel off cover member; the continuous section of closed cell foam having a number of slots formed into a lower portion thereof for allowing urine to flow therethrough and prevent puddling of urine from occurring; the urine collection opening being sized to fit entirely over a pubic hair covered area of a female user.

Accordingly, a non-invasive urine collection device for females is provided. The non-invasive urine collection device for females includes an adhesive covered, flexible film patient attachment structure, a flexible plastic film urine collection funnel member and a disposable urine collection bottle; the adhesive covered, flexible film patient attachment structure having a urine collection opening formed therethrough that is reinforced around an internal perimeter edge thereof by a continuous section of closed cell foam and an exterior perimeter edge thereof totally surrounded by the adhesive covered, flexible film patient attachment structure; the flexible plastic film urine collection funnel member having a top edge in connection with the urine collection opening of the patient attachment structure such that a urine collecting cavity of the urine collection funnel member is in connection with the urine collection opening and a bottom urine discharge fitting formed through a bottom thereof in connection with a first end of a flexible plastic urine transfer tube; the disposable urine collection bottle being in fluid connection with a second end of the urine transfer tube; the adhesive covered, flexible film patient attachment structure being covered with a peel off cover member; the continuous section of closed cell foam having a number of slots formed into a lower portion thereof for allowing urine to flow therethrough and prevent puddling of urine from occurring; the urine collection opening being sized to fit entirely over a pubic hair covered area of a female user.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

EXEMPLARY MODE FOR CARRYING OUT THE INVENTION

Figure 1:
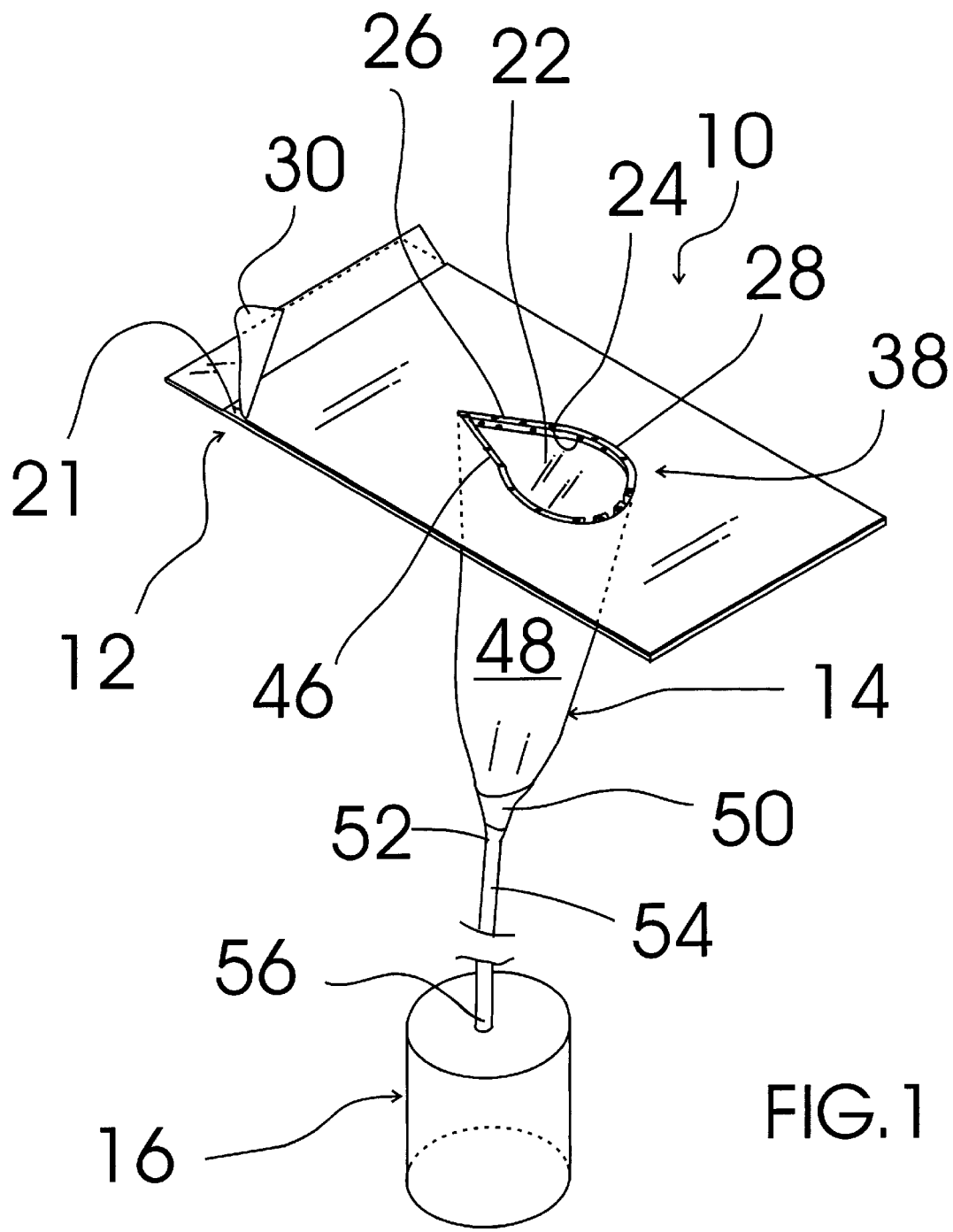
FIG. 1 is a perspective view of an exemplary embodiment of the non-invasive urine collection device for females of the present invention showing the adhesive covered, flexible film patient attachment structure with a urine collection opening formed therethrough and reinforced around an internal perimeter edge thereof supported by a continuous section of closed cell foam and an external perimeter edge thereof being totally surrounded by the adhesive covered, flexible film patient attachment structure; the flexible plastic film urine collection funnel member having a top edge in connection with the urine collection opening of the patient attachment structure such that a urine collecting cavity of the urine collection funnel member is in connection with the urine collection opening and a bottom urine discharge fitting formed through a bottom thereof in connection with a first end of a flexible plastic urine transfer tube; and a disposable urine collection bottle in fluid connection with a second end of the urine transfer tube; the adhesive covered, flexible film patient attachment structure being covered with a peel off cover member; the continuous section of closed cell foam having a number of slots formed into a lower portion thereof for allowing urine to flow therethrough and prevent puddling of urine from occurring; the urine collection opening being sized to fit entirely over a pubic hair covered area of a female user.
Figure 2:
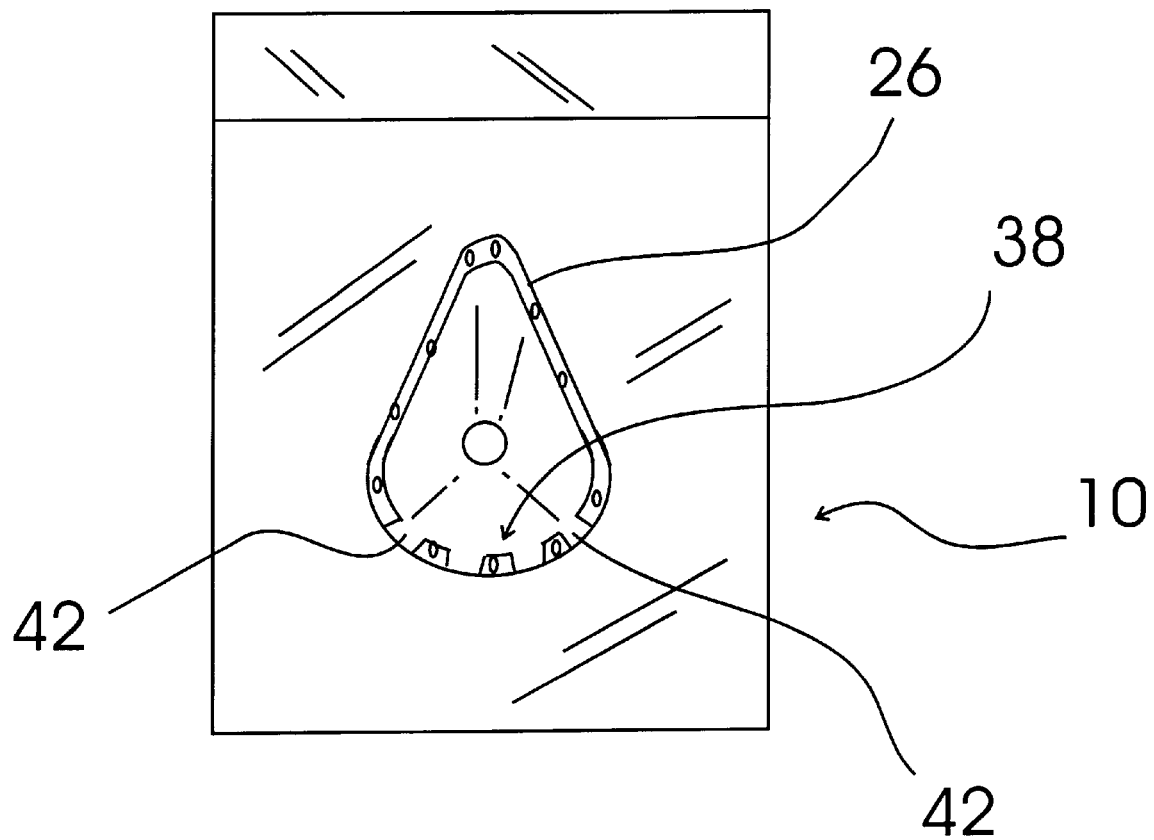
FIG. 2 is a top plan view of the non-invasive urine collection device for females of FIG. 1.

FIGS. 1 and 2 show various aspects of an exemplary embodiment of the non-invasive urine collection device for females of the present invention generally designated 10. Non-invasive urine collection device for females 10 includes an adhesive covered, flexible film patient attachment structure, generally designated 12; a flexible plastic film urine collection funnel member, generally designated 14; and a disposable urine collection bottle, generally designated 16.

Adhesive covered, flexible film patient attachment structure 12 has a plastic film substrate 18 that is covered with a medical skin securable adhesive layer 21 and through which a urine collection opening 22 is formed. Urine collection opening 22 is sized to entirely cover the pubic hair region of a female and has an internal perimeter edge 24 that is reinforced and supported in an open configuration with a continuous section of closed cell foam 26 and an exterior perimeter edge 28 thereof that is totally surrounded by adhesive covered, flexible film patient attachment structure 12. In use, the user peels off a disposable peel away cover member 30 that is placed over adhesive layer 21 during construction and places the pubic hair region into urine collection opening 22 and contacts adhesive layer 21 to the skin surrounding the pubic hair covered area to sealing attach collection device 10 in place to collect urine eliminated in the normal manner. A bottom section 38 of continuous section of closed cell foam 26 is provided with a number of slots 42 to allow urine to flow through slots 42 to prevent urine from puddling.

Flexible plastic film urine collection funnel member 14 has a top edge 46 in connection with urine collection opening 22 of patient attachment structure 12 such that a urine collecting cavity 48 of urine collection funnel member 14 is in connection with urine collection opening 22 and a bottom urine discharge fitting 50 formed through a bottom thereof in connection with a first end 52 of a flexible plastic urine transfer tube 54. Disposable urine collection bottle 16 is in fluid connection with a second end 56 of urine transfer tube 16.

It can be seen from the preceding description that a non-invasive urine collection device for females has been provided.

It is noted that the embodiment of the non-invasive urine collection device for females described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A non-invasive urine collection device for females comprising:

an adhesive covered, flexible film patient attachment structure;

a flexible plastic film urine collection funnel member; and a disposable urine collection bottle;

said adhesive covered, flexible film patient attachment structure having a urine collection opening formed therethrough that is reinforced around an internal perimeter edge thereof by a continuous section of closed cell foam and an exterior perimeter edge thereof totally surrounded by said adhesive covered, flexible film patient attachment structure;

said flexible plastic film urine collection funnel member having a top edge in connection with said urine collection opening of said patient attachment structure such that a urine collecting cavity of said urine collection funnel member is in connection with said urine collection opening and a bottom urine discharge fitting formed through a bottom thereof in connection with a first end of a flexible plastic urine transfer tube;

said disposable urine collection bottle being in fluid connection with a second end of said urine transfer tube;

said adhesive covered, flexible film patient attachment structure being covered with a peel off cover member;

said continuous section of closed cell foam having a number of slots formed into a lower portion thereof for allowing urine to flow therethrough and prevent puddling of urine from occurring.

\* \* \* \* \*